(12) United States Patent
Ninos et al.

(10) Patent No.: US 12,130,251 B2
(45) Date of Patent: Oct. 29, 2024

(54) METHOD FOR OPERATING A GAS SENSOR DEVICE AND GAS SENSOR DEVICE FOR ASCERTAINING PIECES OF INFORMATION ABOUT AN AIR QUALITY

(71) Applicant: Robert Bosch GmbH, Stuttgart (DE)

(72) Inventors: Alexandros Ninos, Tuebingen (DE); Christoph Brueser, Reutlingen (DE)

(73) Assignee: ROBERT BOSCH GMBH, Stuttgart (DE)

( * ) Notice: Subject to any disclaimer, the term of this patent is extended or adjusted under 35 U.S.C. 154(b) by 833 days.

(21) Appl. No.: 17/258,405

(22) PCT Filed: Jul. 11, 2019

(86) PCT No.: PCT/EP2019/068669
§ 371 (c)(1),
(2) Date: Jan. 6, 2021

(87) PCT Pub. No.: WO2020/016091
PCT Pub. Date: Jan. 23, 2020

(65) Prior Publication Data
US 2021/0293733 A1    Sep. 23, 2021

(30) Foreign Application Priority Data

Jul. 20, 2018  (DE) ...................... 10 2018 212 154.0

(51) Int. Cl.
*G01N 27/12*    (2006.01)
*G01N 33/00*    (2006.01)

(52) U.S. Cl.
CPC ....... *G01N 27/124* (2013.01); *G01N 33/0027* (2013.01)

(58) Field of Classification Search
CPC ............... G01N 27/123; G01N 27/124; G01N 33/0062; G01N 33/0032; G01N 33/0073; G01N 2033/0068; G01N 33/0027
See application file for complete search history.

(56) References Cited

U.S. PATENT DOCUMENTS

| | | |
|---|---|---|
| 4,775,838 A | 10/1988 | Mizuta et al. |
| 2010/0089122 A1 | 4/2010 | Abdullah et al. |

(Continued)

FOREIGN PATENT DOCUMENTS

| | | |
|---|---|---|
| CN | 103477220 A | 12/2013 |
| CN | 106053546 A | 10/2016 |

(Continued)

OTHER PUBLICATIONS

International Search Report for PCT/EP2019/068669, Issued Oct. 17, 2019.

(Continued)

*Primary Examiner* — Paul M. West
(74) *Attorney, Agent, or Firm* — NORTON ROSE FULBRIGHT US LLP; Gerard A. Messina

(57) ABSTRACT

A method for operating a gas sensor device for ascertaining information about an air quality. The method includes: providing a gas sensor device including at least one gas-sensitive electrical sensor resistor, a heater for the controlled heating of the sensor resistor, a detection device for detecting the resistance value of the sensor resistor, and a signal processing device for the sensor signal; heating the sensor resistor using the heater alternatingly in a first heating mode in a first operating phase and a second heating mode in a second operating phase, each heating mode including a sequence of heating pulses so that the sensor resistor is heated at predetermined temporal intervals for a predetermined duration to a predetermined operating temperature, an essentially identical operating temperature being selected (Continued)

for the at least two different heating modes; detecting the resistance value of the sensor resistor and generating a sensor signal.

14 Claims, 4 Drawing Sheets

(56) References Cited

U.S. PATENT DOCUMENTS

2016/0216227 A1 7/2016 Boni
2021/0270760 A1* 9/2021 Sai ................ G01N 27/128

FOREIGN PATENT DOCUMENTS

| CN | 106770500 A | 5/2017 |
|---|---|---|
| DE | 19959925 A1 | 6/2001 |
| JP | H1073551 A | 3/1998 |
| WO | 2009068405 A1 | 6/2009 |

OTHER PUBLICATIONS

Kunt T., et al., "Optimization of Temperature Programmed Sensing for Gas Identification Using Micro-Hotplate Sensors," Sensors and Actuators B: Chemical, vol. 53, Issue 1-2, 1998, pp. 24-43.

Ding J., et al., "Surface State Trapping Models for SNO2-Based Microhotplate Sensors," Sensors and Actuators B: Chemical, vol. 77, Issue 3, 2001, pp. 597-613.

Simon I., et al., "Micromachined Metal Oxide Gas Sensors: Opportunities to Improve Sensor Performance," Sensors and Actuators B: Chemical, vol. 73, Issue 1, 2001, pp. 1-26.

Urasinska-Wojcik B., et al., "Identification of H2S Impurity in Hydrogen Using Temperature Modulated Metal Oxide Resistive Sensors With a Novel Signal Processing Technique," IEEE Sensors Letters, IEEE, vol. 1, Issue 4, 2017, pp. 1-4. <https://ieeexplore.ieee.org/stamp/stamp.jsp?arnumber=7942142> Downloaded Dec. 16, 2020.

Burgues J., et al., "Discontinuously Operated Mox Sensors for Low Power Applications," 2017 ISOCS/IEEE International Symposium on Olfaction and Electronic Nose (ISOEN), 2017, pp. 1-3. <https://www.javierburgues.com/publication/burgues-2017-discontinuously/burgues-2017-discontinuously.pdf> Downloaded Dec. 16, 2020.

Jaegle M., et al., "Micromachined Thin Film SN02 Gas Sensors in Temperature-Pulsed Operation Mode," Sensors and Actuators, B. 57, 1999, pp. 130-134. <https://coek.info/queue/pdf-micromachined-thin-film-sno2-gas-sensors-in-temperature-pulsed-operation-mode-.html> Downloaded Dec. 16, 2020.

Dinko Oletic et al., "Energy-Efficient Atmospheric Co Concentration Sensing With On-Demand Operating Mox Gas Sensor," IEEE Sensors 2014 Proceedings, 2014, pp. 1-4.

Bicelli S., et al., "Model and Experimental Characterization of the Dynamic Behavior of Low-Power Carbon Monoxide MOX Sensors Operated With Pulsed Temperature Profiles," IEEE Transactions on Instrumentation and Measurement, BD. 58, NR. 5, 2009, pp. 1324-1332. <https://www.academia.edu/15673382/Model_and_Experimental_Characterization_of_the_Dynamic_Behavior_of_Low_Power_Carbon_Monoxide_MOX_Sensors_Operated_With_Pulsed_Temperature_Profiles>.

* cited by examiner

METHOD FOR OPERATING A GAS SENSOR DEVICE AND GAS SENSOR DEVICE FOR ASCERTAINING PIECES OF INFORMATION ABOUT AN AIR QUALITY

FIELD

The present invention relates to a method for operating a gas sensor device and to a gas sensor device for ascertaining pieces of information about an air quality.

BACKGROUND INFORMATION

Conventional gas sensors may be utilized to determine an air quality, for example, an air quality within a closed space (IAQ indoor air quality). Such gas sensors usually include a sensitive layer or paste, which is able to change its electrical resistance as a function of a concentration of chemically oxidizing or reducing gases, for the sensitive layer. One family of gases frequently encountered in interior spaces are the so-called VOCs (Volatile Organic Compounds). The sensor signal, in particular, a resistance value of the gas-sensitive material, may show an unstable behavior over long periods of time (longer than one day) and it is usually difficult to reproduce or determine the cause of the resistance change over the long time span, in particular, if the gas sensor remains switched off over a long period of time (longer than one day). As a result, it is usually only insufficiently possible to recognize whether the observed resistance change has been caused by an actual change of the gas concentrations in the ambient air or by intrinsic sensor effects.

A gas sensor including a metal oxide layer, which may be heated with heat pulses of varying duration, is described in U.S. Patent Application Publication No. US 2016/0216227 A1.

SUMMARY

The present invention provides a method for operating a gas sensor device, and a gas sensor device for ascertaining pieces of information about an air quality.

Preferred refinements of the present invention are described herein.

A main feature of the present invention is to specify a gas sensor device, which may be operated in various heating modes of an electrical resistor, advantageously of its gas-sensitive material, and which may enable an improved way and greater meaningfulness about the inference of resistance changes on the external influences (gas content) at the resistor, in order to be able to better determine and more exactly identify a cause of the resistance change.

According to an example embodiment of the present invention, a provision of a gas sensor device including at least one gas-sensitive electrical sensor resistor, including a heating means (i.e., a heater) for the controlled heating of the sensor resistor, including a detection device for detecting the resistance value of the sensor resistor and including a signal processing device for the sensor signal; a heating of the sensor resistor using the heating means alternatingly in at least one first heating mode in a first operating phase and in at least one second heating mode in a second operating phase, each heating mode including a sequence of heating pulses so that the sensor resistor is heated in predetermined temporal intervals for a predetermined duration to a predetermined operating temperature, an essentially identical operating temperature being selected for the at least two different heating modes; and a detection of the resistance value of the sensor resistor and a generation of a sensor signal on the basis of this resistance value during the first and second operating phase take place in the method for operating a gas sensor device for ascertaining pieces of information about an air quality.

The scanning signal is advantageously necessary in order to even be able to measure the gas sensor, i.e., the electrical sensor resistor. The scanning signal may be provided by an energy source, for example, a battery or a grid and, for example, via a control unit.

The resistance value is detected and the sensor signal is generated advantageously by the detection device. The sensor signal is advantageously processable by the signal processing device.

The resistor advantageously includes a gas-sensitive material, advantageously a layer, which may be accessible for the ambient air. The gas sensor device, including the heating means, the resistor, the detection device and the signal processing device may be advantageously situated in a portable housing. The operating phases, advantageously their durations and the duration of the heating pulses and the establishment of the operating temperature, may be established by a control unit for the gas sensor device, which may include such a control unit. The sensor signal may be advantageously output/generated as a digital signal, as a voltage, or as a current.

A resistance value known from the structure of the resistor or known via previous calibration measurements including an air quality known and prevailing at this time, i.e., including a content of oxidizing or reducing gases then prevailing (at the time of the calibration measurement) in the ambient air, may be established as a reference value. For example, it may be assumed at one measuring point in time of the calibration measurement that the ambient air exhibits an average purity. The resistance values ascertained at later points in time may then be identified and stored as better or poorer air values depending on the deviation of the resistance value, the content of a particular oxidizing or reducing gas being capable of serving as a basis for the assumption of the air as good or poor.

The measured resistance advantageously provides a conclusion about a concentration of a gas in the ambient air and the measurement is advantageously also a function of the temperature of the sensor and of the air as well as of the relative humidity in the air.

The first and the second heating mode may alternatingly take place, respectively once or respectively multiple times in alternating succession. The first operating phase is advantageously configured to operate the heating means in a particular pulse mode (duration and/or time interval) and the second operating phase is advantageously configured to operate the heating means in a pulse mode differing therefrom (duration and/or time interval).

Dependencies of the measurement on an individual behavior of the resistance value for each gas sensor; on a continuous contamination of the gas-sensitive material, which may cause a drift of the sensitivity (impairment) over time; and changes of the relative humidity may be observable. By means of the operation of the gas sensor device with the alternating heat modes, it is advantageously possible to draw an exact conclusion about the actual conditions of the air, since local and/or short-term effects may be recognized and disregarded (filtered) with the aid of comparison values from the different heating phases, advantageously via the signal processing device.

It is further also possible that the heating means may also operate a third or further heating modes, which may differ in duration, pulse mode, or operating temperature.

According to one preferred specific embodiment of the method in accordance with the present invention, the sensor signal is processed by the signal processing device after detection, an air quality of ambient air relative to an air reference value for the resistor being deduced from the sensor signal.

According to one preferred specific embodiment of the method in accordance with the present invention, the temporal interval between the heating pulses of the first and/or of the second heating mode is constant in each case.

According to one preferred specific embodiment of the method in accordance with the present invention, the duration of the heating pulses of the first and/or of the second heating mode is constant in each case.

According to one preferred specific embodiment of the method in accordance with the present invention, the first and the second heating mode differ by temporal intervals between the heating pulses.

This advantageously means the intervals between the heating pulses of a respective heating mode.

According to one preferred specific embodiment of the method in accordance with the present invention, the first and the second heating mode differ by the duration of the heating pulses.

This advantageously means the duration of the heating pulses of a respective heating mode.

According to one preferred specific embodiment of the method in accordance with the present invention, the detection takes place during the heating pulses, and only when the gas-sensitive electrical resistor is heated to the operating temperature.

According to one preferred specific embodiment of the method in accordance with the present invention, the detection takes place at the end of the heating pulses of the respective heating mode.

The actual detection of the resistance value takes place advantageously only at the end of a heating mode.

According to one preferred specific embodiment of the method in accordance with the present invention, at least one reference value is determined in each operating phase based on the sensor signal and in each case, the reference values of two successive operating phases are compared with one another, a comparison value being determined from the reference values and a piece of information about an air quality being ascertained with the aid of the comparison value.

A comparison value corresponds, for example, to a resistance value and may be set as a comparison for further measured resistance values at other times and conditions.

According to one preferred specific embodiment of the method of the present invention, the comparison values are each determined on the basis of the sensor signal at the end of an operating phase.

The comparison value advantageously corresponds to the resistance value at the end of a heating mode and advantageously serves as a comparison value for further and subsequent determinations (detection) of the resistance value of subsequent heating modes.

According to one preferred specific embodiment of the method in accordance with the present invention, a difference and/or a quotient is/are formed from the comparison values of successive operating phases.

According to an example embodiment of the present invention, the gas sensor device for ascertaining pieces of information about an air quality includes at least one gas-sensitive electrical sensor resistor; a heating means (i.e., a heater) for alternatingly heating the sensor resistor in at least one first heating mode in a first operating phase and in at least one second heating mode in a second operating phase; a detection device, which is configured to detect a resistance value of the sensor resistor and to generate a sensor signal during the first and second operating phase; a signal processing device via which the sensor signal is processable; and a control unit, which is configured to control the heating means for heating the gas-sensitive electrical sensor resistor in such a way that the sensor resistor is alternatingly heated at least in the first heating mode and at least in the second heating mode so that in each case an operating phase in a first heating mode is followed by an operating phase in another second heating mode, each heating mode including a sequence of heating pulses, which heat the sensor resistor at predefined temporal intervals for a predetermined duration to a predetermined operating temperature, the operating temperature of the at least two different heating modes being essentially identical.

According to one preferred specific embodiment of the gas sensor device in accordance with the present invention, the signal processing device is configured to deduce an air quality of ambient air relative to an air reference value for the resistor based on the sensor signal.

According to one preferred specific embodiment of the gas sensor device in accordance with the present invention, the signal processing device includes a memory that includes stored air reference values for the resistance value and air quality values assigned to the air reference values.

In addition to the reference values, comparison values from the heating modes may also be stored. The reference values for a particular air quality (air reference value), for example, for determining whether an air quality at an ascertained concentration value of a gas is good or poor, may be newly stored for a particular reference value during the subsequent (measuring) operation of the gas sensor device, i.e., for example, the previous memory value for the best measured air may be corrected.

The gas sensor device is further characterized also by the features and advantages previously cited in connection with the method and vice versa.

Further features and advantages of specific embodiments of the present invention result from the following description with reference to the figures.

BRIEF DESCRIPTION OF THE DRAWINGS

The present invention is described in greater detail below with reference to the exemplary embodiments specified in the schematic figures.

In the figures, identical reference numerals refer to identical or functionally identical elements.

DETAILED DESCRIPTION OF EXAMPLE EMBODIMENTS

Figure 1:
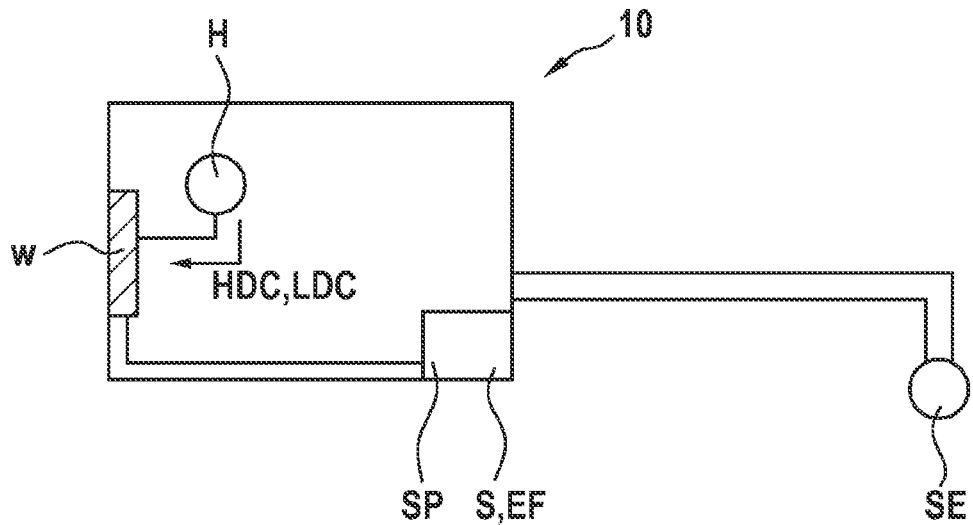
FIG. 1 schematically shows a representation of a gas sensor device according to one exemplary embodiment of the present invention.

FIG. 1 schematically shows a representation of the gas sensor device according to one exemplary embodiment of the present invention.

Gas sensor device 10 for ascertaining pieces of information about an air quality includes at least one gas-sensitive electrical sensor resistor W; a heating means (i.e., a heater) H for alternatingly heating sensor resistor W in at least one first heating mode HDC in a first operating phase and in at least one second heating mode LDC in a second operating phase; a detection device EF, which is configured to detect a resistance value of sensor resistor W and to generate a sensor signal during the first and second operating phase; a signal processing device S via which the sensor signal is processable; and a control unit SE, which is configured to control heating means H for heating gas-sensitive electrical resistor W in such a way that the sensor resistor is alternatingly heated at least in first heating mode HDC and at least in second heating mode LDC so that in each case an operating phase in a first heating mode is followed by a heating phase in another second heating mode, each heating mode including a sequence of heating pulses, which heat sensor resistor W at predetermined temporal intervals for a predetermined duration to a predetermined operating temperature, the operating temperature of the at least two different heating modes being essentially identical.

The electrical resistor advantageously includes a gas-sensitive layer or paste, for example, a VOC (Volatile Organic Compound). The gas-sensitive material may include, for example, $SnO_2$ or Zno, i.e., tin oxide or zinc oxide.

Gas sensor device 10 may be connected to a control unit SE, which is able to control the operating phases and the heating modes, the detection device and the signal processing device as well as a management of the reference values stored in memory S.

Electrical resistor W may be situated at an outer side of a housing of gas sensor device 10, advantageously in such a way that the gas-sensitive layer or paste may be in contact with the ambient air.

Figure 2:
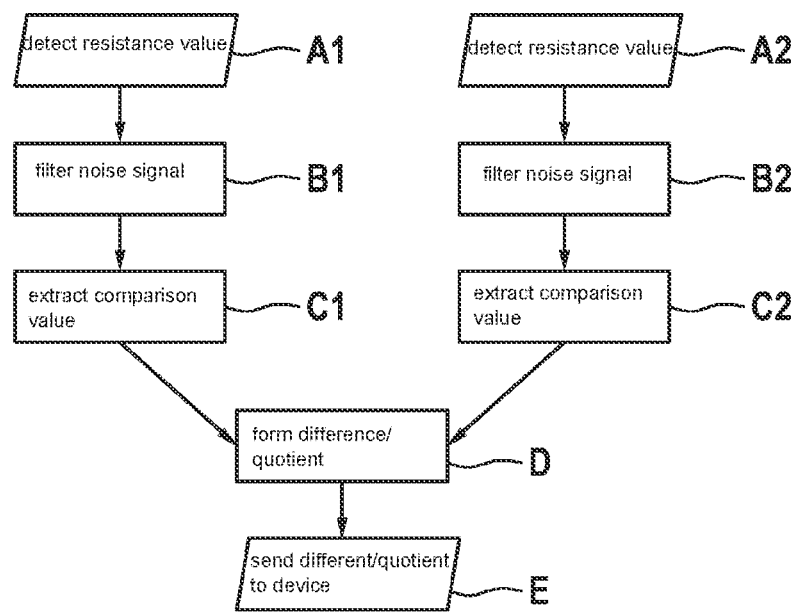
FIG. 2 schematically shows a block diagram of a sequence of the signal processing according to one exemplary embodiment of the present invention.

FIG. 2 schematically shows a block diagram of a sequence of the signal processing according to one exemplary embodiment of the present invention.

A flow chart of a pre-processing (in the control unit or in the signal processing device) at the gas sensor device is advantageously shown, for example, to the left for data (measured values) from the first heating mode and to the right for data (measured values) from the second heating mode. In a step A1 and A2, a resistance value from the resistor may be detected during the heating mode. In a step B1 and B2, a filter step may take place in order to filter out a noise signal, in a step C1 and C2, the last point of the measurement in a heating phase may be extracted as a comparison value (a comparison value for the resistance value may be determined on the basis of the sensor signal).

In this case, at least one reference value may be determined in each operating phase based on the sensor signal and in each case the reference values from two successive operating phases may be compared with one another, a comparison value being determined from the reference values, and a piece of information about an air quality being ascertained with the aid of the comparison value.

Taking both comparison values from the two heating modes (successive) into account, a difference and/or a quotient may be formed in step D from the comparison values of successive operating phases. In step E, this difference and/or the quotient may be sent to a device for studying the base measurement (baseline tracker, assessment relative to a stored air reference value), for example, inside in the signal processing device, and evaluated. In this case, an actually measured resistance by the device for studying the base measurement relative to an air reference value may also be assessed or a new air reference value may be set as a new orientation value for good or poor air, for exactly this gas sensor device. For example, the highest value of past times may be consistently stored, since the level of the resistance value may be equated with the purity of the air. The signal processing device may then assess each ascertained resistance value relative to this air reference value relating to its air quality.

Figure 3:
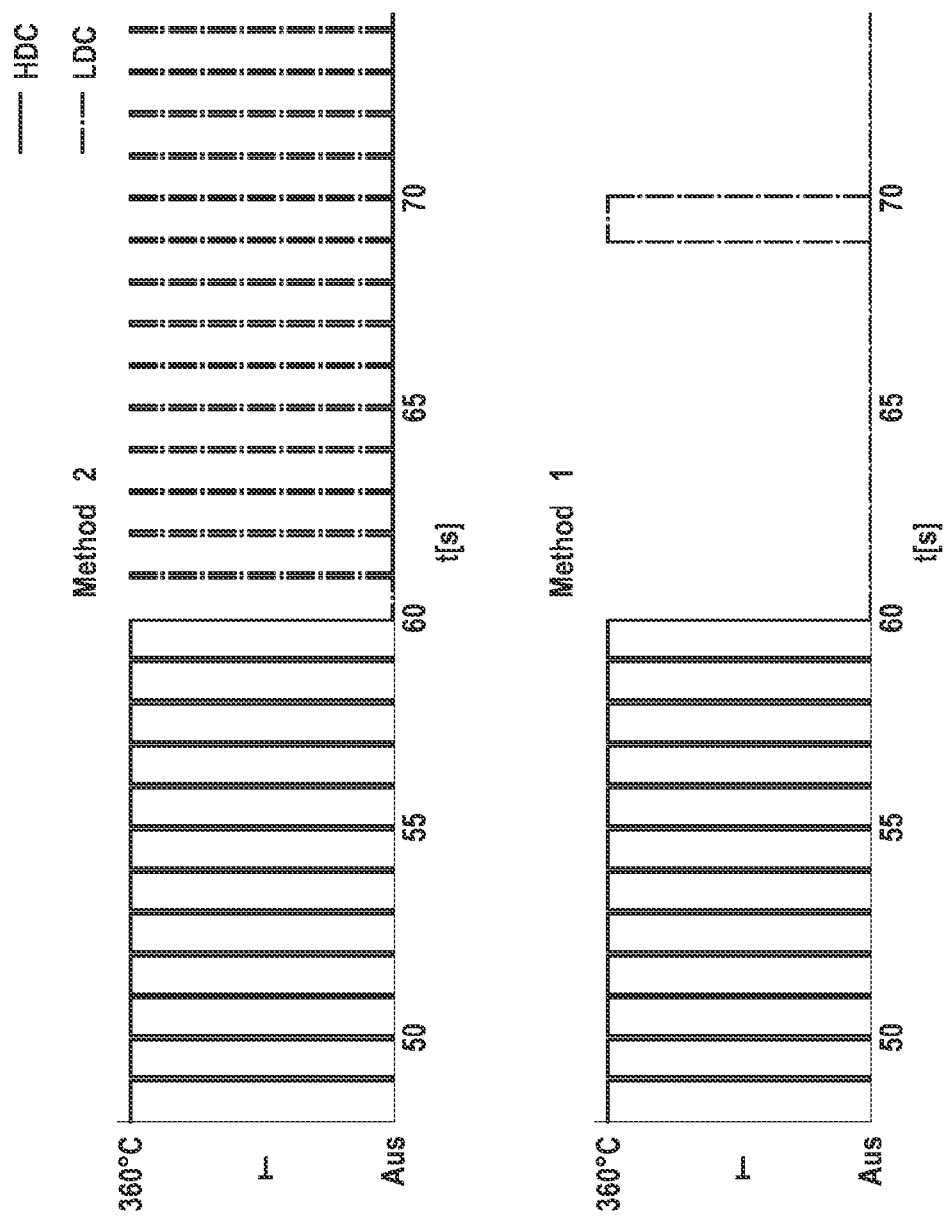
FIG. 3 shows a temporal sequence of heating pulses in one exemplary embodiment of the method according to the present invention.

FIG. 3 shows a temporal sequence of heating pulses in one exemplary embodiment of the method according to the present invention.

Figure 4:
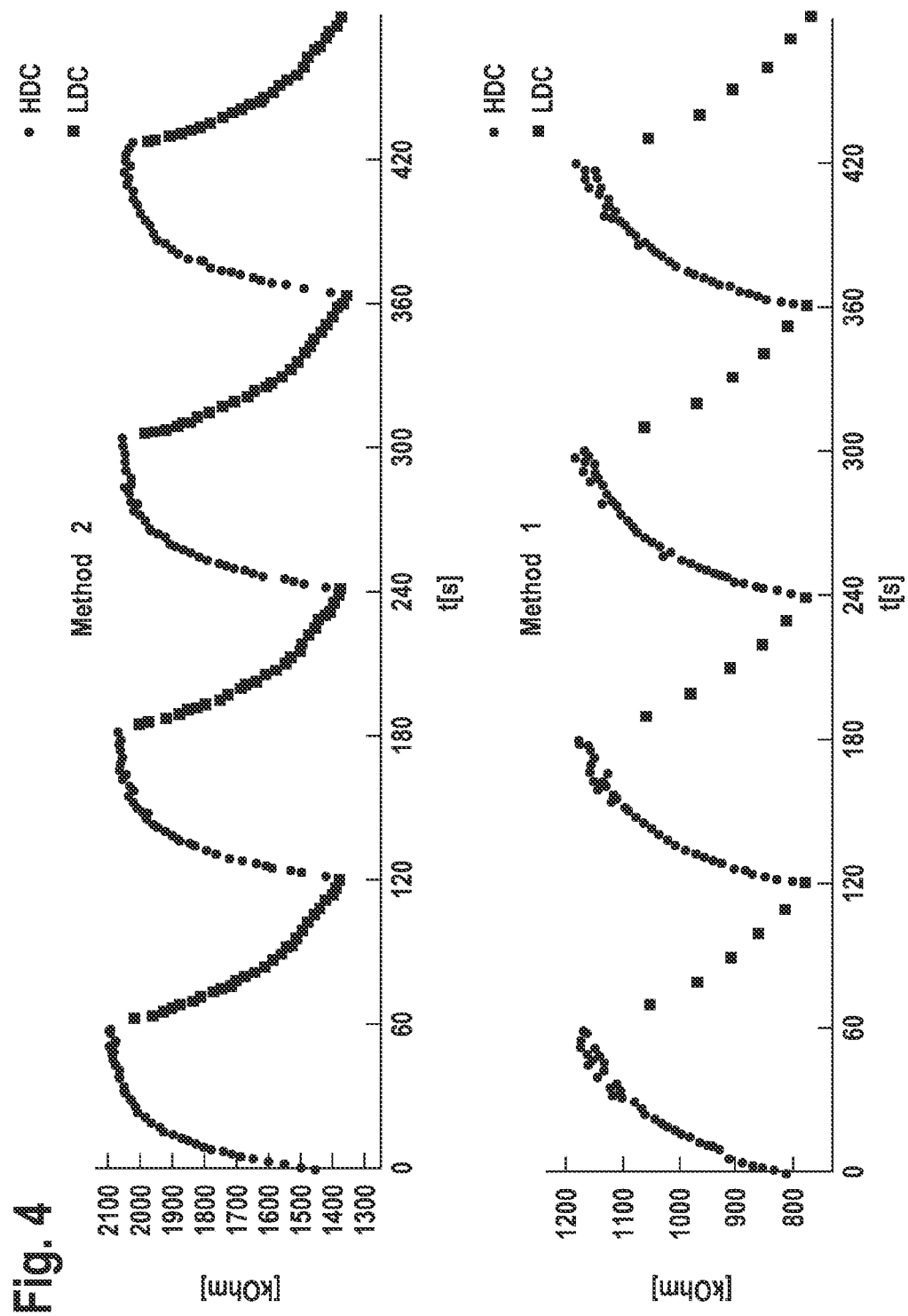
FIG. 4 shows a temporal sequence of resistance values in one exemplary embodiment of the method according to the present invention.

FIG. 3 shows the sequence of heating pulses in the two methods according to FIG. 4. The upper figure shows a profile of the heating time for the first heating mode (to the left) and for the second heating mode (to the right) including a duration (period of the heating mode) and individual heating pulses, which may differ in their duration for the first and second heating mode.

The lower figure shows a profile of the heating time for the first heating mode (to the left) and for the second heating mode (to the right) including a duration (period of the heating mode) and individual heating pulses, which may be identical in their duration for the first and for the second heating mode.

The heating means in this case is advantageously so efficient that the operating temperature is reached in merely a fraction of a pulse length (also the shortest). By measuring the resistance, or further semiconductor materials, at an operating temperature, undesirably influencing temperature effects on the measurement may be filtered out during the signal processing or may not even occur in the first place. Any slow signal changes, for example, in constant gas surroundings, may be based on slow chemical reactions and may appear during and outside heating modes. In the first heating mode, if a high rate of heating pulses is able to take place, chemical processes may dominate, which take place at operating temperature, in the second heating mode, if a low rate of heating pulses is able to take place, chemical processes (and thermal drift movements, for example, as changes of the sensor properties or of the resistor with the temperature) are dominating, which take place at room temperature. A comparison of both heating modes may be advantageously utilized for considering chemical processes taking place only at operating temperature.

FIG. 4 shows a temporal sequence of resistance values in one exemplary embodiment of the method according to the present invention.

A profile of the resistance values over time according to a second method is shown in the upper figure, when first heating mode HDC is operated for a duration (period of the heating mode) of advantageously 60 seconds and the second heating mode for a duration of advantageously 60 seconds. According to the second method, the operation of the heating means in a pulsed heating mode advantageously has a heating time relative to the duration of a period of the heating mode (first and second), which may be identical for the first and for the second heating mode.

A scanning time for the gas sensor is, for example, 1 second in the first heating mode and 10 seconds in the second heating mode. For example, the heating time in the first heating mode is 90% of the time of a period of the first heating mode and the heating time in the second heating mode is 9% of the time of a period of the second heating mode (relative to the period duration). As a result of the different scanning time, it is then possible to achieve an actual heating time in a period of the heating mode of, for example, 900 ms (relative heating time*scanning time) and an actual heating time in a period of the second heating mode of also 900 ms.

The lower figure shows a profile of the resistance values over time according to a first method when first heating mode HDC is operated for a duration (period of the heating mode) of advantageously 60 seconds and the second heating mode for a duration of advantageously 60 seconds. According to the first method, the operation of the heating means in a pulsed heating operation advantageously has a heating time relative to the duration of a period of the heating mode (first and second), which may be different for the first and for the second heating mode.

A scanning time for the gas sensor is, for example, 1 second, and is the same in method 1 for both heating modes. For example, the heating time in the first heating mode is 90% of the time of a period of the first heating mode and the heating time in the second heating mode is 9% of the time of a period of the second heating mode. As a result of the equal scanning time, it is then possible to achieve an actual heating time in a period of the first heating mode of for example, 900 ms (relative heating time*scanning time) and an actual heating time in a period of the second heating mode of 900 ms.

In this case, the resistor is advantageously heated in both heating modes to the same operating temperature, for example, of 360° C.

The heating modes advantageously result in a periodic behavior of the gas sensor device with marked changes in the signal at transition points between the heating modes.

The signal processing beyond the heating modes, i.e., a comparison of both heating modes for similarities yields results in the signal profile, which may be advantageously independent with respect to the individual behavior of the electrical resistor in different gas sensors, to a dependency of the signal with respect to drifts (changes) in the sensitivity over time, and to variations in relative humidity and temperature.

Figure 5:
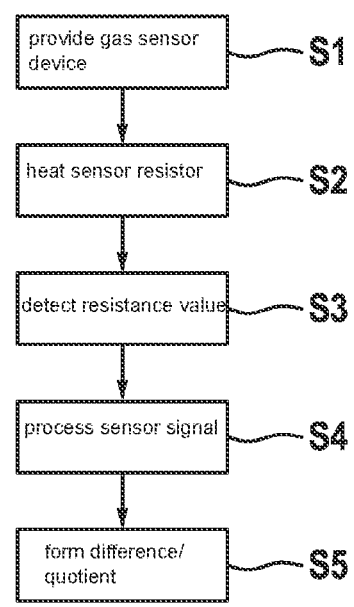
FIG. 5 shows a sequence of method steps according to one exemplary embodiment of the present invention.

FIG. 5 shows a sequence of method steps according to one exemplary embodiment of the present invention.

In the method for operating a gas sensor device for ascertaining pieces of information about an air quality, a provision S1 of a gas sensor device including at least one gas-sensitive electrical sensor resistor, including a heating means for the controlled heating of the sensor resistor, including a detection device for detecting the resistance value of the sensor resistor, and including a signal processing device for the sensor signal; a heating S2 of the sensor resistor using the heating means alternatingly in at least one first heating mode in a first operating phase and in at least one second heating mode in a second operating phase, each heating mode including a sequence of heating pulses so that the sensor resistor is heated at predetermined temporal intervals for a predetermined duration to a predetermined operating temperature, an essentially identical operating temperature being selected for the at least two different heating modes; and a detection S3 of the resistance value of the sensor resistor and generation of a sensor signal on the basis of this resistance value during the first and second operating phase take place.

Although the present invention has been completely described based on the preferred exemplary embodiment, it is not restricted thereto, but is modifiable in a variety of ways.

What is claimed is:

1. A method for operating a gas sensor device for ascertaining pieces of information about an air quality, the method comprising the following steps:
    providing a gas sensor device including at least one gas-sensitive electrical sensor resistor, a heater configured for controlled heating of the sensor resistor, a detection device configured to detect a resistance value of the sensor resistor, and a signal processing device configured to process a sensor signal;
    heating the sensor resistor using the heater alternatingly in at least one first heating mode in a first operating phase and in at least one second heating mode in a second operating phase, each of the first heating mode and second heating mode including a sequence of heating pulses, so that the sensor resistor is heated at predetermined temporal intervals for a predetermined duration to a predetermined operating temperature, an identical operating temperature being selected for the at least first heating mode and the second heating mode, the first heating mode and the second heating mode being different from one another;
    detecting the resistance value of the sensor resistor; and
    generating the sensor signal based on the detected resistance value during the first operating phase and the second operating phase.

2. The method as recited in claim 1, wherein after the detecting, the sensor signal is processed by the signal processing device, and an air quality of ambient air relative to an air reference value for the resistor is deduced from the sensor signal.

3. The method as recited in claim 1, wherein a temporal interval between the heating pulses of the first heating mode and/or of the second heating mode is constant in each case.

4. The method as recited in claim 1, wherein a duration of the heating pulses of the first heating mode and/or of the second heating mode is constant in each case.

5. The method as recited in claim 1, wherein the first heating mode and the second heating mode differ from one another by temporal intervals between the heating pulses.

6. The method as recited in claim 1, wherein the first heating mode and the second heating mode differ from one another by a duration of the heating pulses.

7. The method as recited in claim 1, wherein the detecting takes place during the heating pulses, and only when the gas-sensitive electrical resistor is heated to the predetermined operating temperature.

8. The method as recited in claim 7, wherein the detecting takes place at an end of the heating pulses of each of the first and second heating modes.

9. The method as recited in claim 1, wherein in each of the operating phase and second operating phase, at least one reference value is determined based on the sensor signal and, in each case, reference values from two successive operating phases are compared with one another, a comparison value being determined from the reference values, and a piece of information about an air quality being ascertained using the comparison value.

10. The method as recited in claim 9, wherein the comparison values are each determined based the sensor signal at an end of an operating phase.

11. The method as recited in claim 9, wherein a difference and/or a quotient is formed from the comparison values of successive operating phases.

12. A gas sensor device for ascertaining pieces of information about an air quality, comprising:
- at least one gas-sensitive electrical sensor resistor;
- a heater configured to alternatingly heat the sensor resistor in at least one first heating mode in a first operating phase and in at least one second heating mode in a second operating phase;
- a detection device configured to detect a resistance value of the sensor resistor and to generate a sensor signal during the first operating phase and the second operating phase;
- a signal processing device configured to process the sensor signal; and
- a control unit configured to control the heater to heat the gas-sensitive electrical resistor in such a way that the sensor resistor is heated alternatingly at least in the first heating mode and at least in the second heating mode, so that, in each case, an operating phase in the first heating mode is followed by an operating phase in the second heating mode, each heating mode including a sequence of heating pulses, which heat the sensor resistor at predetermined temporal intervals, for a predetermined duration to a predetermined operating temperature, the operating temperature of the at least two different heating modes being identical.

13. The gas sensor device as recited in claim 12, wherein the signal processing device is configured to deduce from the sensor signal an air quality of ambient air relative to an air reference value for the resistor.

14. The gas sensor device as recited in claim 13, wherein the signal processing device includes a memory including stored air reference values for the resistance value and air quality values assigned to the air reference values.

* * * * *